(12) United States Patent  
Salomonsson et al.

(10) Patent No.: US 8,562,827 B2
(45) Date of Patent: Oct. 22, 2013

(54) CHROMATOGRAPHY COLUMN ASSEMBLY COMPRISING A FIXTURE FOR A PLASTIC MESH

(75) Inventors: Daniel Salomonsson, Uppsala (SE); Petter Bennemo, Uppsala (SE); Per Uselius, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 0 days.

(21) Appl. No.: 13/634,035

(22) PCT Filed: Mar. 10, 2011

(86) PCT No.: PCT/SE2011/050261
§ 371 (c)(1),
(2), (4) Date: Sep. 11, 2012

(87) PCT Pub. No.: WO2011/112144
PCT Pub. Date: Sep. 15, 2011

(65) Prior Publication Data
US 2013/0001147 A1    Jan. 3, 2013

(30) Foreign Application Priority Data
Mar. 12, 2010    (SE) ........................................ 1000230

(51) Int. Cl.
*B01D 15/08*    (2006.01)
(52) U.S. Cl.
USPC ........................................ 210/198.2; 210/656

(58) Field of Classification Search
USPC .............. 210/198.2, 232, 238, 282, 450, 635, 210/656; 96/101, 105, 106
See application file for complete search history.

(56) References Cited

U.S. PATENT DOCUMENTS

| | | | | |
|---|---|---|---|---|
| 3,474,908 | A | * | 10/1969 | Catravas ..................... 210/198.2 |
| 4,280,905 | A | * | 7/1981 | Gunkel et al. ............... 210/198.2 |
| 4,361,482 | A | * | 11/1982 | Teetz et al. .................. 210/198.2 |
| 4,451,364 | A | * | 5/1984 | Higgins et al. .............. 210/198.2 |
| 4,563,275 | A | * | 1/1986 | McEachern ................. 210/198.2 |
| 5,167,810 | A | * | 12/1992 | Vassarotti et al. ........... 210/198.2 |
| 5,423,982 | A | * | 6/1995 | Jungbauer et al. ........... 210/198.2 |
| 6,139,732 | A | * | 10/2000 | Pelletier ..................... 210/198.2 |
| 6,171,486 | B1 | * | 1/2001 | Green et al. ................. 210/198.2 |
| 6,352,266 | B1 | | 3/2002 | Rigoli |
| 2005/0242018 | A1 | | 11/2005 | Hodgin et al. |
| 2006/0156918 | A1 | | 7/2006 | Dahl |
| 2006/0213824 | A1 | * | 9/2006 | Higgins et al. ............. 210/198.2 |

FOREIGN PATENT DOCUMENTS

| | | |
|---|---|---|
| EP | 0 008 921 | 3/1980 |
| EP | 008921 | * 3/1980 |
| GB | 1 297 647 | 11/1972 |
| GB | 2 110 951 | 6/1983 |
| WO | WO 96/10451 | 4/1996 |
| WO | WO 2009/041877 | 4/2009 |

* cited by examiner

*Primary Examiner* — Ernest G Therkorn

(57) ABSTRACT

In a chromatography column, at least one plastic retaining mesh is attached to a distributor plate using a fixture element comprising an elongated edge that penetrates into the plastic mesh to ensure sealing and to prevent radial movement of the plastic mesh.

8 Claims, 9 Drawing Sheets

CHROMATOGRAPHY COLUMN ASSEMBLY COMPRISING A FIXTURE FOR A PLASTIC MESH

CROSS-REFERENCE TO RELATED APPLICATIONS

This application is a filing under 35 U.S.C. 371 of international application number PCT/SE2011/050261, filed Mar. 10, 2011, published on Sep. 15, 2011 as WO 2011/112144, which claims priority to application number 1000230-1 filed in Sweden on Mar. 12, 2010.

TECHNICAL FIELD

The present invention relates generally to separation and specifically to chromatographic separation of biomolecules. More particularly the invention relates to fixtures for plastic meshes in chromatography columns and column assemblies comprising such fixtures.

BACKGROUND OF THE INVENTION

Chromatography columns may be used in industrial processes to purify process liquids and separate substances of interested from process liquids. Prior art chromatography columns comprise a column wall in the form of hollow column tube which is connected to a removable upper end plate assembly and a removable lower end plate assembly. One end plate assembly is provided with a process fluid inlet arrangement, typically comprising an inlet pipe and an inlet valve and the other end plate assembly is provided with a process fluid outlet arrangement, typically comprising an outlet pipe and an outlet valve. Each end of the column tube is usually provided in the interior of the column with a removable distributor plate. These inlet and outlet distributor plates may be attached to the respective end plate assembly or the upper distributor plate may be arranged to be movable towards or away from the end plate assembly. During use, the space in the column between the distributor plates is usually filled with a chromatography medium. A retaining mesh is normally provided between each distribution system and the media in order to prevent media particles from escaping the column. The inlet distributor plate is intended to distribute incoming fluid evenly over the surface of the media at the inlet end of the column while the outlet distributor plate is intended to collect fluid evenly from the surface of the media at the outlet end of the column Such a column may weigh several tons.

The retaining meshes extend across substantially the whole internal diameter of the column and are normally fixed along the outer perimeter of the column and at the center of the column. The meshes can be prepared from woven threads of either metals or polymers or they can be made from sintered particles. They can also be multilayer constructions of e.g. several woven meshes joined by sintering. During maintenance of the column it is desirable that the retaining mesh can be easily exchanged for a new one with an arrangement providing good sealing and no stagnant zones that may impair sanitation of the column EP008921(A1) describes a structure with snap ring action for fixing a polyethylene sinter mesh but this solution does not satisfy current needs for sealing and sanitation. There is thus a need for further improvements in this regard.

BRIEF DESCRIPTION OF THE INVENTION

One aspect of the present invention is to provide a secure, non-leaking and sanitary attachment of a plastic mesh to a distributor plate or a support ring. This is achieved with a fixture element for securing a plastic mesh to a distributor plate in a chromatography column assembly, wherein said fixture element comprises an edge intended to penetrate into the plastic mesh. It is also achieved with a chromatography column assembly comprising at least one plastic mesh and at least one fixture element attaching said plastic mesh to a distributor plate wherein said fixture element comprises an edge penetrating into the plastic mesh to provide sealing and to prevent radial movement of the plastic mesh. In other words, an elongated edge on the fixture element penetrates into the plastic mesh during assembly and provides sealing and fixation of the plastic mesh with minimal stagnant dead-leg volumes.

DEFINITIONS

The term "mesh" means herein any porous material in sheet form that can be used to retain chromatography media in a column. Meshes can be made from e.g. woven threads, entanglements of non-woven threads, sintered particles, stretched sheets etc and the materials used can be e.g. metals, polymers, glasses or ceramics. In a plastic mesh, the material comprises a polymer.

DETAILED DESCRIPTION OF THE INVENTION

Figure 1:
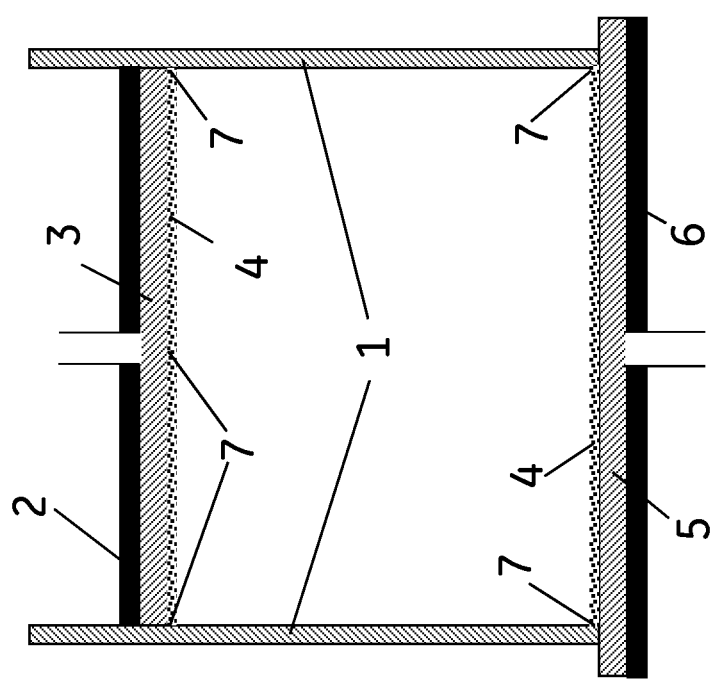
FIG. 1 shows a schematic view of a chromatography column in cross section.
Figure 2:
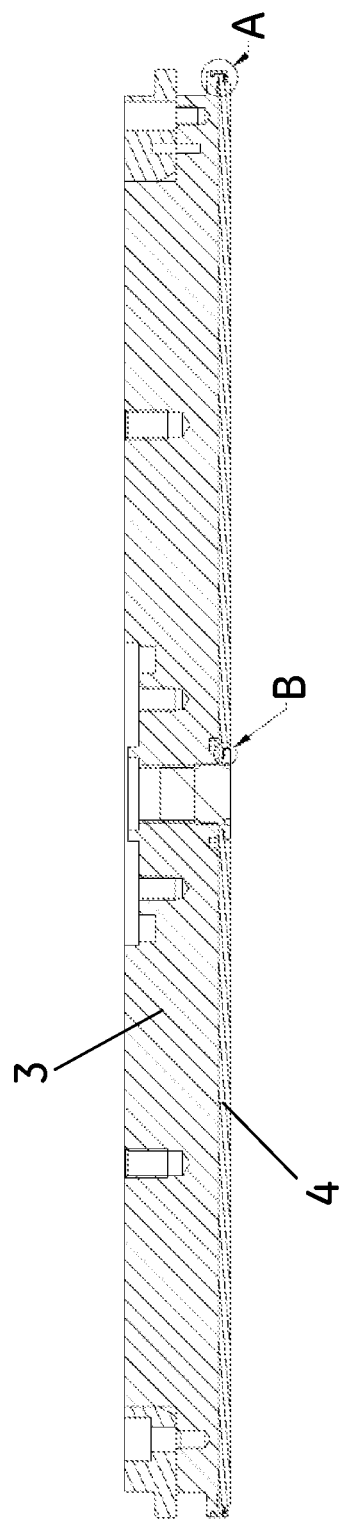
FIG. 2 shows an adaptor distributor plate and a plastic mesh according to one embodiment of the invention.

One embodiment of the invention, is a chromatography column assembly wherein the edge 9, 12, 13, 15, 16 of the fixture element 7 penetrates at least 0.1 mm or at least 0.5 mm into the plastic mesh 4. FIG. 1 shows a schematic view of a chromatography column with column tube 1, adaptor backing plate 2, adaptor distributor plate 3, plastic meshes 4, bottom distributor plate 5, bottom backing plate 6 and fixture elements 7.

In one embodiment the plastic mesh 4 is a plastic sinter mesh. Sinter meshes are typically prepared by heat compression of polymer powders in molds, allowing the sintering of the powder particles into a cohesive porous material. The pore size of the sinter mesh can be selected to be sufficiently small to retain the chromatography media particles but not so small as to give a large pressure drop over the mesh. Pore sizes between 7 and 150 microns can be suitable for use in the invention. The thickness of the sinter mesh can be from about 0.75 to about 10 mm.

In one embodiment the plastic mesh 4 comprises a polyolefin material, such as polyethylene. Examples of polyolefin materials are polyethylene, polypropylene, polybutylene, poly-alfaolefins, cycloolefin polymers and any copolymers of ethylene, propylene, butylene, alfaolefins or cycloolefins. Specific examples of polyethylene are high density polyethylene (HDPE), low density polyethylene (LDPE), linear low density polyethylene (LLDPE), ultralow density polyethylene (ULDPE) and ultrahigh molecular weight polyethylene (UHMWPE). Examples of commercially available polyethylene sinter meshes are Vyon PE from Porvair PLC (UK) and POREX PE from Porex Corp (US). An advantage of using polyethylene is that it is a resilient flexible material available in high purity and it is soft enough to allow penetration of the fixture element edge.

Figure 3:
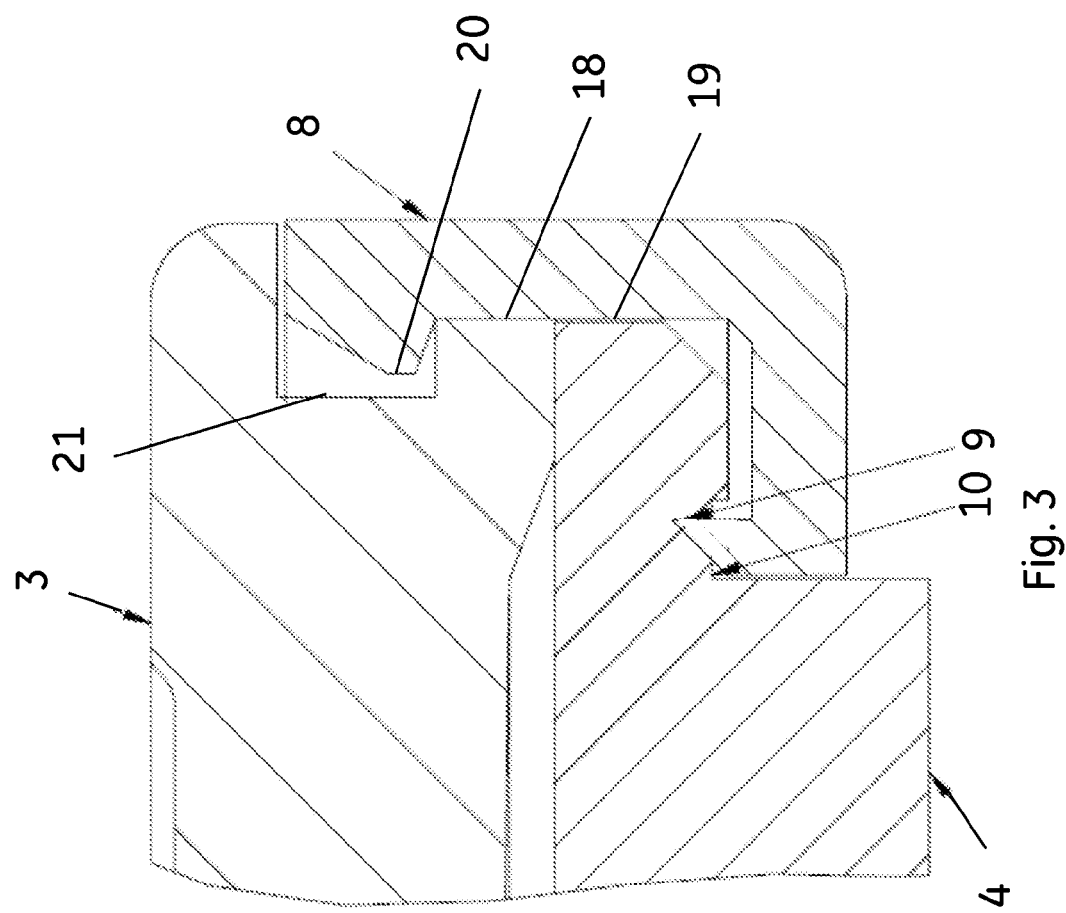
FIG. 3 shows an enlargement of area A in FIG. 2, according to one embodiment of the invention.
Figure 9:
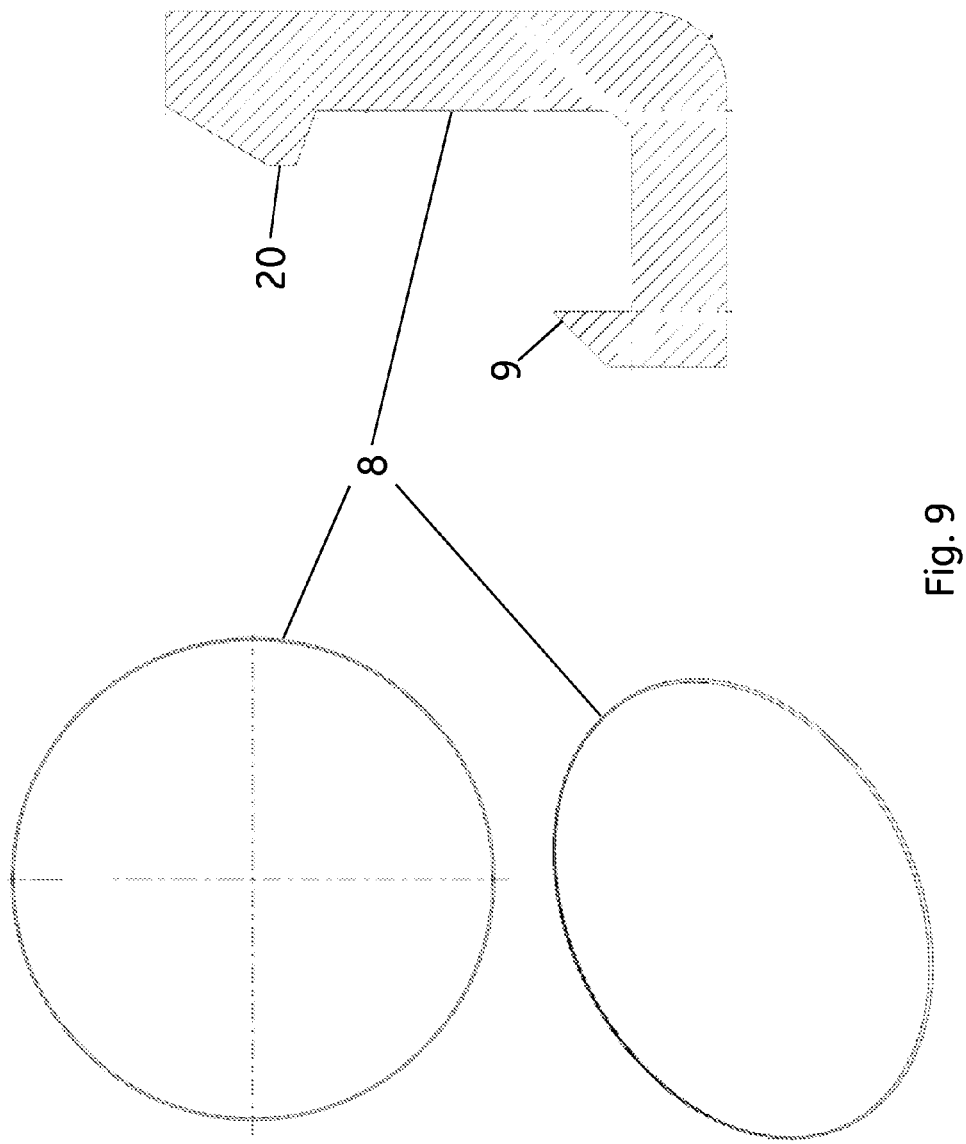
FIG. 9 shows a snap ring with an edge, according to one embodiment of the invention.

In one embodiment, illustrated by FIGS. 3 and 9, the fixture element comprises a snap ring 8. The snap ring can be prepared from an elastically deformable material such as a polyolefin, e.g. polyethylene, so that it can be radially extended, applied over the perimeter 18 of the distributor plate and the perimeter 19 of the plastic mesh and then allowed to snap back, fixing the plastic mesh to the distributor plate. A snap-on protrusion 20 on the snap ring can then fit into a recess 21 on the perimeter of the distributor and keep the snap ring in an axial position. The edge 9 on the snap ring may penetrate into the plastic mesh 4 during application of the snap ring 8, but it is also possible to ensure penetration by applying axial pressure on the snap ring 8 with a suitable tool after application of the snap ring. The plastic mesh 4 may further comprise a groove 10 for partial accommodation of the snap ring edge 9, to allow for easier assembling. The edge will then penetrate into the mesh starting from the bottom of the groove 10.

Figure 4:
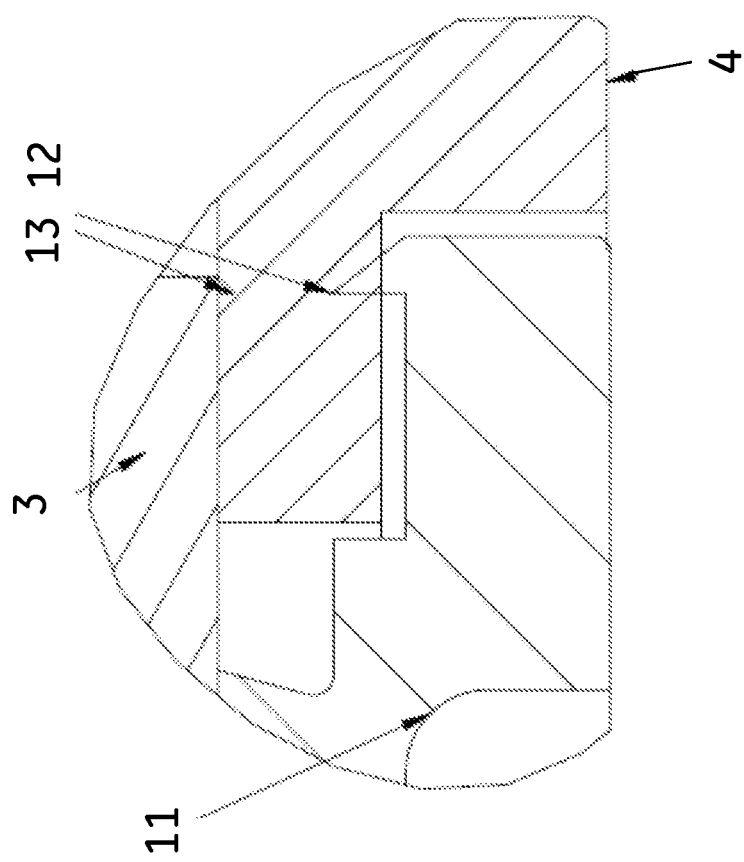
FIG. 4 shows an enlargement of area B in FIG. 2, according to one embodiment of the invention.
Figure 5:
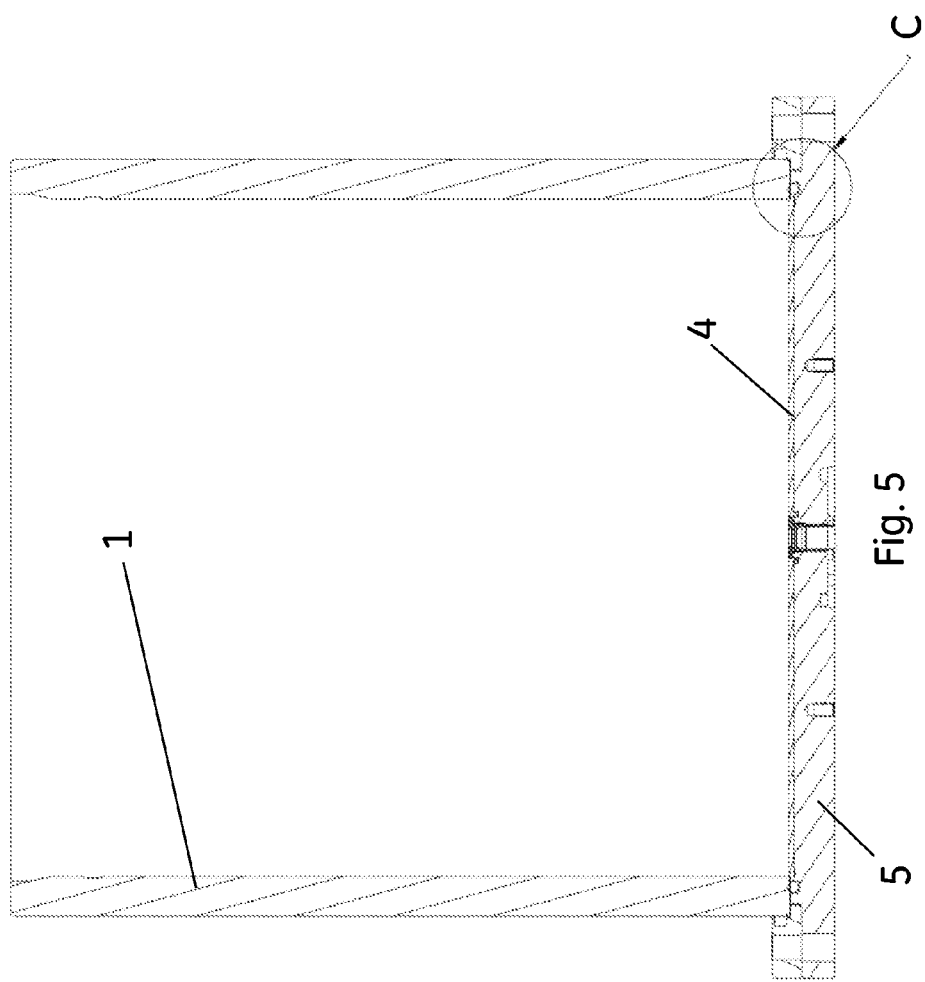
FIG. 5 shows an overview of a column tube with a plastic retaining mesh and a bottom distributor plate, according to one embodiment of the invention.

In one embodiment, illustrated by FIG. 4, the fixture element comprises a screw 11. The screw can be applied to a threaded hole (not shown) in the center of the distributor plate and the edge 12 can be situated close to the perimeter of the screw 11 in such a way that when the screw is fastened, the edge will cut into the plastic mesh 4 and give the desired sealing and fixation.

Figure 6:
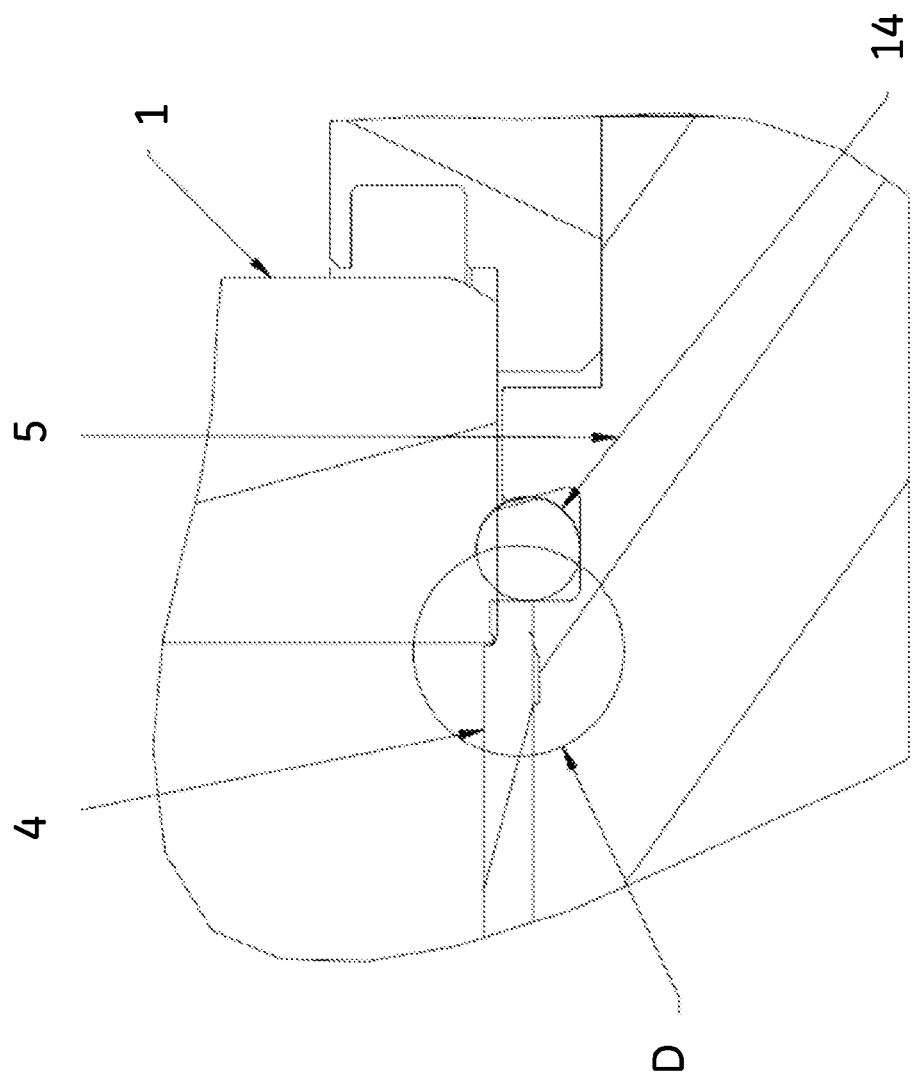
FIG. 6 shows an enlargement of area C in FIG. 5, according to one embodiment of the invention.
Figure 7:
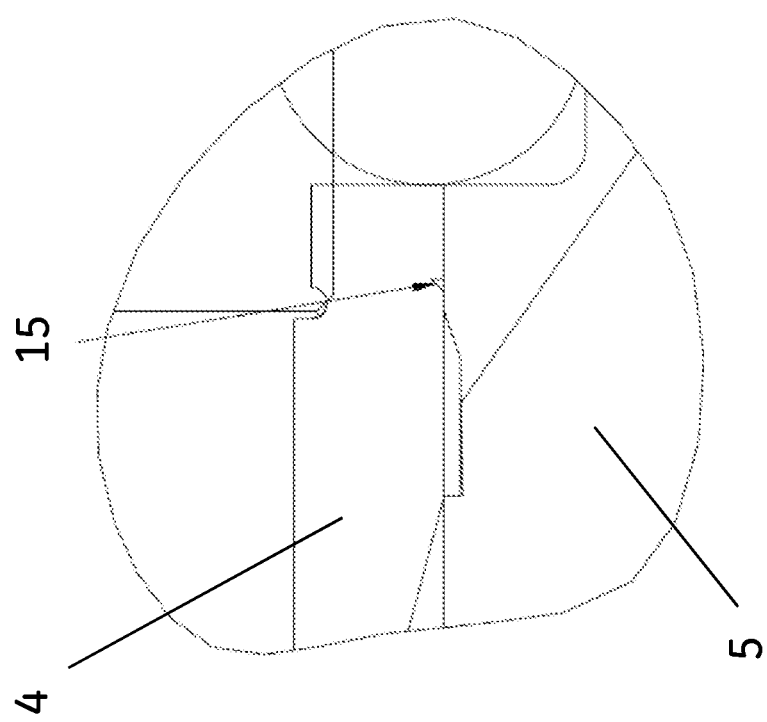
FIG. 7 shows a further enlargement of area D in FIG. 6, according to one embodiment of the invention.

In one embodiment, illustrated by FIGS. 4, 6 and 7 the fixture element comprises an integral feature of a distributor plate 3,5. The integral feature can be an edge 13,15 protruding from the surface of the distributor plate 3,5, so that when the plastic mesh 4 is pressed against the distributor plate, the edge penetrates into the mesh to achieve sealing and fixation. An o-ring 14 can be used to provide additional sealing between the column tube 1 and the bottom distributor plate 5.

In one embodiment the diameter of the plastic mesh 4 is at least 10 cm or at least 40 cm. Handling of larger diameter meshes, which can be difficult using methods known in the art, is facilitated by the fixture elements of the invention. Demands for good sealing and prevention of radial movement are also accentuated for large diameter meshes, making the fixture elements of the invention particularly useful.

In one embodiment the edge 9, 12, 13, 15, 16 on the fixture element 7 has a height of at least 0.2 mm or at least 0.5 mm. An advantage of a high edge is that it ensures a sufficient penetration depth to ensure sealing and fixation.

Figure 8:
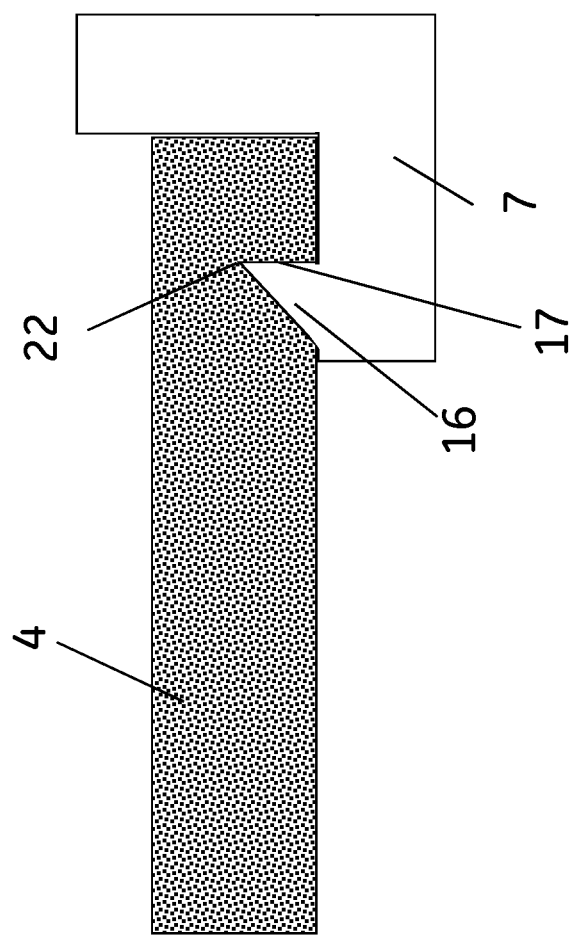
FIG. 8 shows a plastic mesh and a fixture element according to one embodiment of the invention.

In one embodiment, illustrated by FIG. 8, the edge 16 is sharp, with a radius of curvature less than 0.1 mm, such as less than 0.01 mm, at the tip 22. A sharp edge with a low radius of curvature at the tip will facilitate penetration into the plastic mesh.

In one embodiment, illustrated by FIG. 8, the edge 16 has an essentially triangular cross section with one side 17 essentially perpendicular to the plastic mesh 4. An advantage of this is that it improves the radial fixation of the mesh, preventing lateral movement particularly in the direction towards the perpendicular side of the edge.

Other features and advantages of the invention will be apparent from the claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

All patents, patent publications, and other published references mentioned herein are hereby incorporated by reference in their entireties as if each had been individually and specifically incorporated by reference herein. While preferred illustrative embodiments of the present invention are described, one skilled in the art will appreciate that the present invention can be practiced by other than the described embodiments, which are presented for purposes of illustration only and not by way of limitation. The present invention is limited only by the claims that follow.

The invention claimed is:

1. A chromatography column assembly comprising at least one plastic mesh (4) and at least one fixture element (7) attaching said plastic mesh to a distributor plate (3,5), wherein said fixture comprises an edge (9,12,13,15,16) penetrating into the plastic mesh (4) to provide sealing and to prevent radial movement of the plastic mesh.

2. The chromatography column assembly of claim 1, wherein the edge (9,12,13,15,16) penetrates at least 0.1 mm or 0.5 mm into the plastic mesh (4).

3. The chromatography column assembly of claim 1, wherein the plastic mesh (4) is a plastic sinter mesh.

4. The chromatography column assembly of claim 1, wherein the plastic mesh (4) comprises a polyolefin material, such as polyethylene.

5. The chromatography column assembly of claim 1, wherein the fixture element comprises a snap ring (8).

6. The chromatography column assembly of claim 1, wherein the fixture element comprises a screw (11).

7. The chromatography column assembly of claim 1, wherein the fixture element comprises an integral feature of a distributor plate (3,5).

8. The chromatography column assembly of claim 1, wherein the diameter of the plastic mesh (4) is at least 10 cm or at least 40 cm.

\* \* \* \* \*